(12) United States Patent
Hwang (10) Patent No.: US 8,644,567 B2
(45) Date of Patent: Feb. 4, 2014

(54) METHOD FOR ACQUIRING A THREE-DIMENSIONAL IMAGE OF A SET OF TEETH

(75) Inventor: Hyeon Shik Hwang, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 196 days.

(21) Appl. No.: 13/384,159

(22) PCT Filed: Jul. 13, 2010

(86) PCT No.: PCT/KR2010/004533
§ 371 (c)(1),
(2), (4) Date: Jan. 13, 2012

(87) PCT Pub. No.: WO2011/007998
PCT Pub. Date: Jan. 20, 2011

(65) Prior Publication Data
US 2012/0121156 A1 May 17, 2012

(30) Foreign Application Priority Data
Jul. 15, 2009 (KR) .......................... 10-2009-0064647

(51) Int. Cl.
*G06K 9/00* (2006.01)
(52) U.S. Cl.
USPC ....................................................... 382/128
(58) Field of Classification Search
None
See application file for complete search history.

(56) References Cited

U.S. PATENT DOCUMENTS

| 6,243,439 B1 | 6/2001 | Arai et al. | |
| 6,493,415 B1 | 12/2002 | Arai et al. | |
| 8,442,283 B2 * | 5/2013 | Choi | 382/128 |
| 2008/0124681 A1 | 5/2008 | Cha | |
| 2011/0255765 A1 * | 10/2011 | Carlson et al. | 382/131 |

FOREIGN PATENT DOCUMENTS

| JP | 11-253433 A | 9/1999 |
| JP | 2006-034670 A | 2/2006 |
| KR | 10-0854634 B1 | 8/2008 |
| WO | 00-57789 A1 | 10/2000 |

OTHER PUBLICATIONS

International Search Report for PCT/KR2010/004533.
English Translation of Abstract of JP 2006-034670.
English Translation of Abstract of JP 11-253433.
English Translation of Abstract of WO 00-57789.
English Translation of Abstract of KR 10-0854634.

* cited by examiner

*Primary Examiner* — Claire X Wang
(74) *Attorney, Agent, or Firm* — The PL Law Group, PLLC (57) ABSTRACT

The present invention relates to a method for acquiring a 3-Dimensional (3D) image of a set of teeth, and, in particular, to a method for acquiring a 3D image of a set of teeth which can continuously acquire a plurality of 3D images of a set of teeth which show the change of dentition of a patient using only a single Computed Tomography (CT) scan.

16 Claims, 6 Drawing Sheets

METHOD FOR ACQUIRING A THREE-DIMENSIONAL IMAGE OF A SET OF TEETH

CROSS REFERENCE TO RELATED APPLICATION

The present application claims all benefits accruing under 35 U.S.C. §365(c) from the PCT International Application PCT/KR2010/004533, with an International Filing Date of Jul. 13, 2010, which claims the benefit of Korean patent application No. 10-2009-0064647 filed in the US Patent and Trademark Office on Jul. 15, 2009, the entire contents of which are incorporated herein by reference.

BACKGROUND

1. Technical Field

The present invention relates to a method for acquiring a 3-Dimensional (3D) image of a set of teeth, and, in particular, to a method for acquiring a 3D image of a set of teeth which can continuously acquire a plurality of 3D images of a set of teeth which show the change of dentition of a patient using only a single Computed Tomography (CT) scan.

2. Background Art

Images of sets of teeth are images which allow the arrangements of the teeth of patients to be ascertained and have been widely used in the medical fields, including orthodontics, maxillofacial surgery, and physical anthropology.

Furthermore, since the permanent teeth of a person are characterized in that the sizes thereof do not change, the person have a unique set of teeth and teeth are ones of the hardest structures of a human body, images of sets of teeth have been recently utilized usefully in the fields of human identification, security, and forensic medicine.

Figure 1:
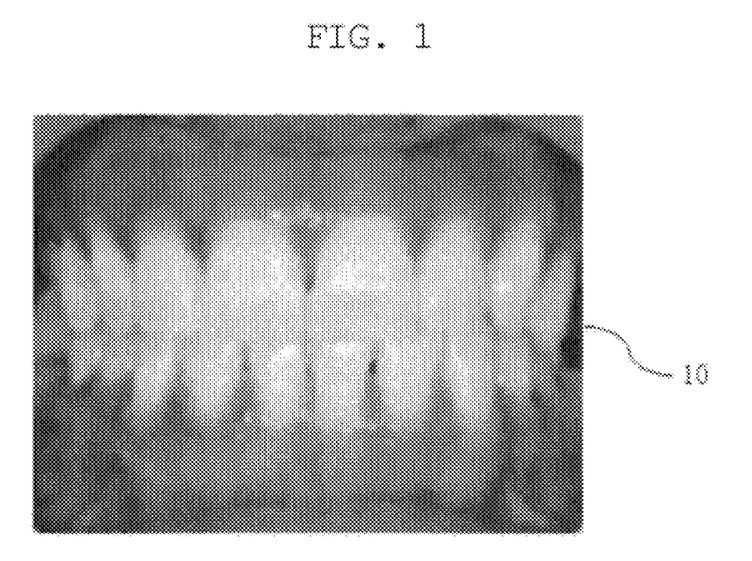
FIG. 1 is a view showing a conventional image of a set of teeth.

FIG. 1 is a view showing a conventional image of a set of teeth.

Referring to FIG. 1, a conventional dentition image 10 is generally acquired as a 2D image using an optical camera.

Furthermore, since the dentition image 10 shows the external side of the teeth, the dentition image 10 is also called a labial side image.

Furthermore, although FIG. 1 shows the labial side image including all of the teeth, this labial side image is substantially acquired by photographing the right side, front side, left side, maxillary occlusal side and mandibular occlusal side of the teeth. Since the upper and lower teeth are occluded with each other, the image is also called a labial side occlusion image.

That is, the conventional dentition image 10 shows the external side (labial side) of the teeth, and therefore enables a practitioner to treat the external side of the teeth or observe the orthodontic status thereof.

Furthermore, although not shown, a conventional image of a set of teeth may be photographed as an image of the inner surface (lingual side) of the teeth.

However, lingual side photographs cannot be taken in a state or occlusion. Therefore, in order to observe lingual occlusion, there is the inconvenience of additionally taking an impression using plaster.

Therefore, a conventional image of a set of teeth has the problem of being unable to provide information about the lingual occlusion viewed from the inner side (lingual side) of teeth and image information about tooth roots as well.

In order to solve the above-described problem, a method of enabling the teeth of a patient to be observed in 3D by taking dental CT scans has been developed. However, this method is problematic in that considerable numbers of CT scans should be taken periodically and repeatedly in order to acquire information about a set of teeth which changes according to growth or treatment.

SUMMARY

The present inventor has studied and made an effort to acquire 3D images of a set of teeth which can provide all information about the labial side, lingual side, and tooth roots of the changing set of teeth of a patient using only a single CT scan. As a result, the inventor developed a technical configuration in which 3D images of a set of teeth can be acquired using changing labial side images only, resulting in the completion of the present invention.

Accordingly, an object of the present invention is to provide a method for acquiring a 3D image of a set of teeth which can acquire 3D images of the changing teeth set of a patient using only a single CT scan.

Another object of the present invention is to provide a method for acquiring a 3D image of a set of teeth which can provide lingual side information and tooth root image information as well as labial side information by acquiring 3D images of a changing set of teeth using only a labial side image in which changes overtime.

Further another object of the present invention is to provide a method for acquiring a 3D image of a set of teeth which can acquire a 3D image of a set of teeth which matches the set of teeth of a patient at high accuracy by acquiring a 3D labial side image by taking a photograph once.

The objects of the present invention are not limited to the above-mentioned objects, and other objects which are not mentioned may be clearly appreciated by those skilled in the art based on the following description.

In order to accomplish the above objects, the present invention provides a method for acquiring a 3D image of a set of teeth, including acquiring 3D tooth images of respective teeth of a patient using a CT scan; acquiring a first labial side image which is an optical image in which a set of teeth of the patient is shown; and acquiring a first 3D dentition image which includes the set of teeth of the first labial side image by integrating the 3D tooth images with the first labial side image and arranging the 3D tooth images in conformity with the set of teeth of the first labial side image.

Furthermore, in order to accomplish the above objects, the present invention provides a method for acquiring a 3D image of a set of teeth, including acquiring a first labial side image which is an optical image in which a set of teeth of a patient is shown; acquiring 3D tooth images of respective teeth of the patient using a CT scan; and acquiring a first 3D dentition image which includes the set of teeth of the first labial side image by integrating the 3D tooth images with the first labial side image and arranging the 3D tooth images in conformity with the set of teeth of the first labial side image.

In a preferred embodiment, the method further includes, after the acquiring the first 3D dentition image, acquiring a second labial side image of the patient after an observation or a treatment period; and acquiring a second 3D dentition image which includes a set of teeth of the second labial side image by integrating the 3D tooth images with the second labial side image and arranging the 3D tooth images in conformity with the set of teeth of the second labial side image.

In a preferred embodiment, the method further includes, after the acquiring the second 3D dentition image, simultaneously displaying the first 3D dentition image and the second 3D dentition image such that a change in the set of teeth between the first 3D dentition image and the second 3D dentition image can be detected.

In a preferred embodiment, each of the labial side images is acquired as a 3D labial side image using a 3D dental camera which includes a plurality of optical cameras and which can photograph all of the teeth of the patient at one time.

Furthermore, in order to accomplish the above objects, the present invention provides a method for acquiring a 3D image of a set of teeth, including acquiring a first 3D dentition image of a patient using a CT scan; acquiring 3D tooth images of respective teeth of the patient by performing tooth segmentation on the first 3D dentition image; acquiring a labial side image which is an optical image in which a set of teeth of the patient is shown after an observation or a treatment period; and acquiring a second 3D dentition image which includes the set of teeth of the labial side image by integrating the 3D tooth images with the labial side image and arranging the 3D tooth images in conformity with the set of teeth of the labial side image.

Furthermore, in order to accomplish the above objects, the present invention provides a method for acquiring a 3D image of a set of teeth, including acquiring a first 3D dentition image of a patient using a CT scan; acquiring a labial side image which is an optical image in which a set of teeth of the patient is shown after an observation or a treatment period; acquiring 3D tooth images of respective teeth of the patient by performing tooth segmentation on the first 3D dentition image; and acquiring a second 3D dentition image which includes the set of teeth of the labial side image by integrating the 3D tooth images with the labial side image and arranging the 3D tooth images in conformity with the set of teeth of the labial side image.

Furthermore, in order to accomplish the above objects, the present invention provides a method for acquiring a 3D image of a set of teeth, including acquiring 3D tooth images of respective teeth of a patient using a CT scan; acquiring a labial side image which is an optical image in which a set of teeth of the patient is shown after an observation or a treatment period; and acquiring a 3D dentition image which includes the set of teeth of the labial side image by integrating the 3D tooth images with the labial side image and arranging the 3D tooth images in conformity with the set of teeth of the labial side image.

The present invention has the following excellent advantages.

First, in accordance with the method for acquiring a 3D image of a set of teeth according to the present invention, all the labial side information, lingual side information and tooth root information about the change of dentition of a patient can be provided using a single CT scan, so that the present invention has the advantage of acquiring 3D images of a set of teeth which can be used for a variety of types of evaluation or analysis.

Furthermore, in accordance with the method for acquiring a 3D image of a set of teeth according to the present invention, 3D labial side images, which are produced by acquiring labial side images, viewed from various angles, using a 3D dental camera at one time, are used, so that the present invention has the advantage of reducing the number of times that an optical picture is taken.

Furthermore, in accordance with the method for acquiring a 3D image of a set of teeth according to the present invention, it is not necessary to additionally take an impression in order to acquire information about lingual occlusion viewed from the lingual side of teeth, so that the present invention has the advantage of reducing the human cost and the pecuniary cost when dental treatment, such as orthodontics, is performed.

Furthermore, in accordance with the method for acquiring a 3D image of a set of teeth according to the present invention, 3D images of a changing set of teeth can be provided using a single CT scan, so that the present invention has the advantage of reducing the amount of radiation to which a patient is exposed.

Furthermore, 3D images of a set of teeth, which are acquired using the method for acquiring a 3D image of a set of teeth according to the invention, can be used to recreate an actual object using a 3D printer, so that the present invention has the advantage of using the method for acquiring a 3D image of a set of teeth to fabricate various types of dental appliances, such as an actual orthodontic appliances, along with a 3D image simulation technique.

BRIEF DESCRIPTION OF DRAWINGS

In the drawings according to the present invention, the same reference numerals are used to designate the components which substantially have the same configurations and functions.

DETAILED DESCRIPTION OF EXEMPLARY EMBODIMENTS

Although, to the maximum extent possible, the terms used in the present invention are selected as general terms that are widely used currently, some of the terms in specific cases have been arbitrarily selected by the applicant. In this case, the meanings of the terms should be construed by taking into consideration not the simple names of the terms but the meanings of the terms described or used in the detailed description of the invention.

Hereinafter, the technical configuration of the present invention will be described in detail with reference to the accompanying drawings and preferred embodiments.

However, the present invention is not limited to the embodiments which will be described herein, and may be embodied in other forms. The same reference numerals designate the same components throughout the specification.

Figure 2:
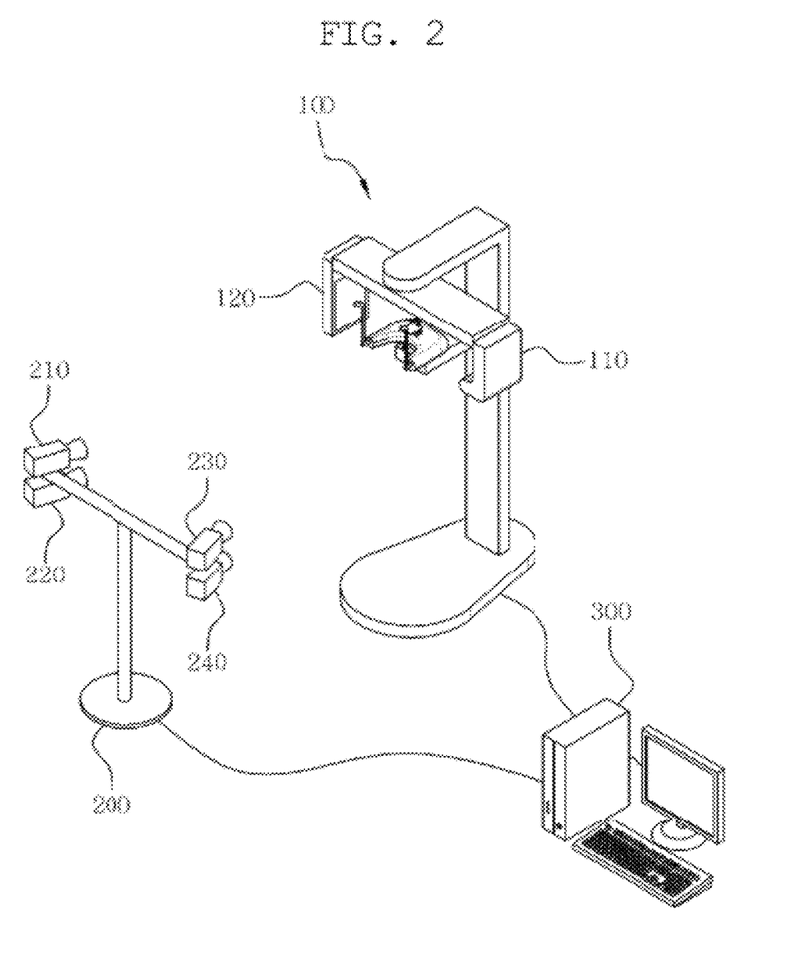
FIG. 2 is a view showing an environment that is required to perform a method for acquiring a 3D image of a set of teeth according to an embodiment of the present invention.
Figure 3:
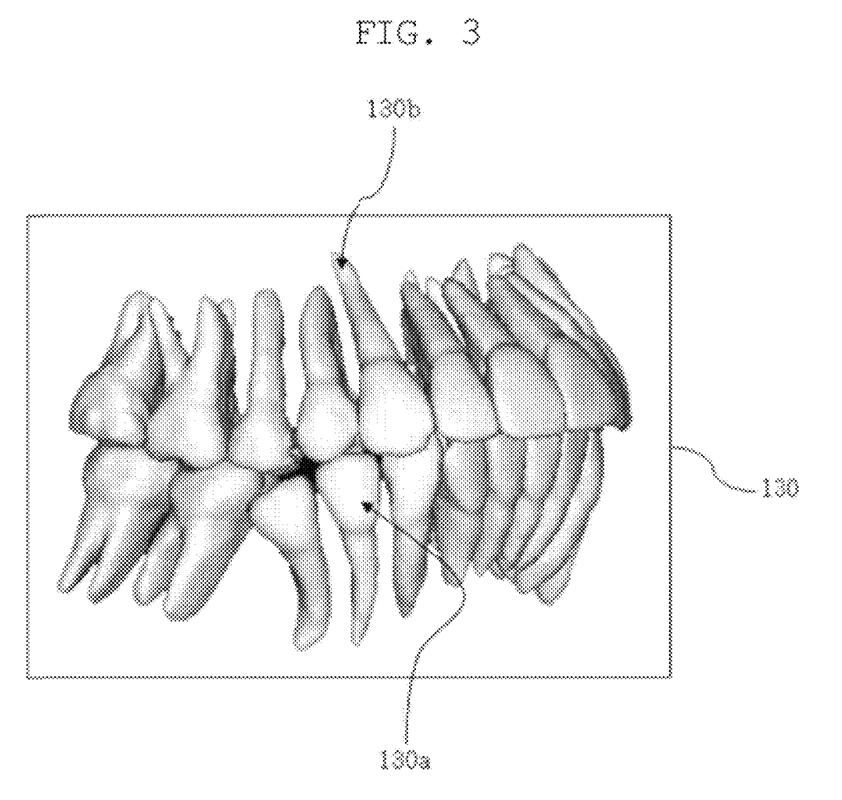
FIG. 3 is a view showing the labial side of a 3D dentition image that is acquired using the method for acquiring a 3D image of a set of teeth according to the embodiment of the present invention.
Figure 4:
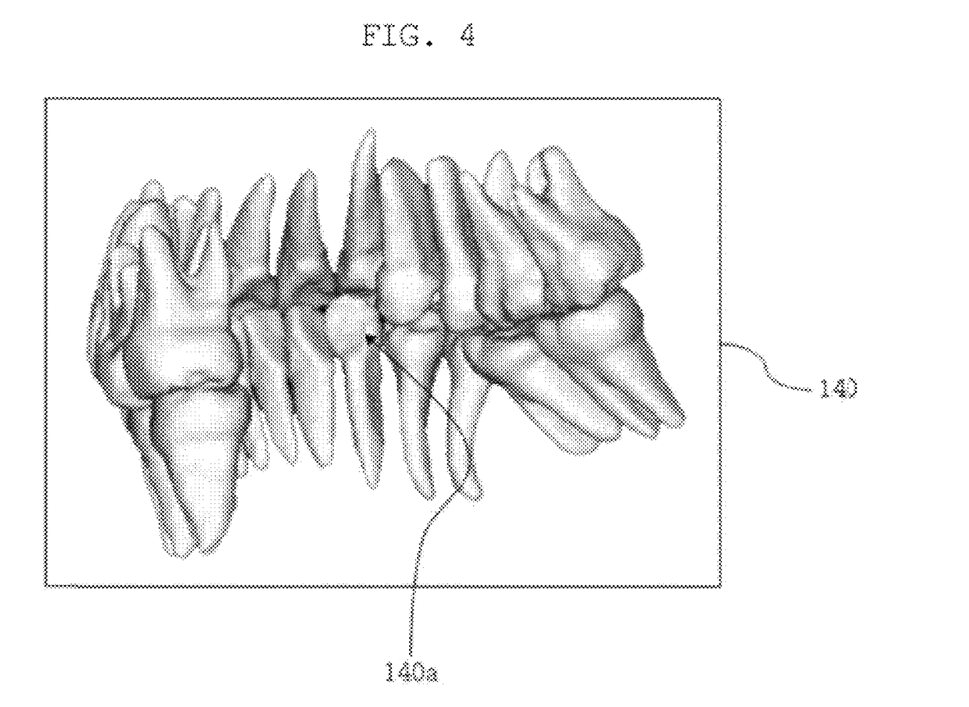
FIG. 4 is a view showing the lingual side of the 3D tooth image that is acquired using the method for acquiring a 3D image of a set of teeth according to the embodiment of the present invention.

FIG. 2 is a view showing an environment that is required to perform a method for acquiring a 3D image of a set of teeth according to an embodiment of the present invention, FIG. 3 is a view showing the labial side of a 3D dentition image that is acquired using the method for acquiring a 3D image of a set of teeth according to the embodiment of the present invention, and FIG. 4 is a view showing the lingual side of the 3D dentition image that is acquired using the method for acquiring a 3D image of a set of teeth according to the embodiment of the present invention.

Referring FIG. 2, a CT scan apparatus 100, a 3D dental camera 200, and an image processing apparatus 300 are provided to perform the method for acquiring a 3D image of a set of teeth according to the embodiments of the present invention.

The CT scan apparatus 100 is configured to include a beam source 110 for radiating X-rays and a sensor 120 capable of receiving the X-rays and acquiring the CT data of the head or dental arch of a patient.

That is, the CT scan apparatus 100 is a dental CT scan apparatus which allows the head of a patient to be positioned between the beam source unit 110 and the sensor 120 and then acquires the CT data of the head or dental arch of the patient.

However, it is apparent that any type of medical CT scan apparatus may be provided as the CT scan apparatus 100 as long as the type of CT scan apparatus can acquire the CT data of the head or dental arch of a patient.

The 3D dental camera 200 is a camera which can photograph all of the teeth of a patient at once, and is configured to include a plurality of optical cameras 210, 220, 230, and 240 for photographing the labial side of the teeth of a patient from different directions.

For example, the 3D dental camera 200 may be configured to include a first optical camera 210 for photographing the labial side of the teeth of a patient from the upper-left direction, a second optical camera 220 for photographing the labial side of the teeth of the patient from the lower-left direction, a third optical camera 230 for photographing the labial side of the teeth of the patient from the upper-right direction, and a fourth optical camera 240 for photographing the labial side of the teeth of the patient from the lower-right direction.

However, any type of 3D dental camera 200 may be provided as the 3D dental camera 200 as long as a 3D labial side image 240 which will be described below can be acquired by photographing the labial side of the teeth of a patient from different directions using at least two optical cameras.

The image processing apparatus 300 is connected to the CT scan apparatus 100 and the 3D dental camera 200, receives CT data acquired by the CT scan apparatus 100 and labial side images 211, 221, 231, and 241 acquired by the 3D dental camera 200, and reconfigures the CT data as 3D images of a set of teeth 130, 140, and reconfigures the labial side images 211, 221, 231, and 241 as a 3D labial side image 250.

Referring to FIGS. 3 and 4, it can be seen that the 3D images of the set of teeth 130 and 140 which are acquired according to the embodiment of the present invention show the lingual side 140a of the teeth of the patient as well as the labial side 130a thereof and further show the shapes of tooth roots 130b accurately.

Therefore, there is an advantage in that the 3D images of the set of teeth 130 and 140 acquired according to the embodiment of the present invention can accurately show the images of the lingual side 140a and tooth roots 130b which cannot be shown by the conventional 2D labial side image 10.

In particular, there is an advantage in that it is not necessary to additionally take an impression because the lingual side 140a shows the configuration of the lingual occlusion of the teeth of the patient.

Figure 5:
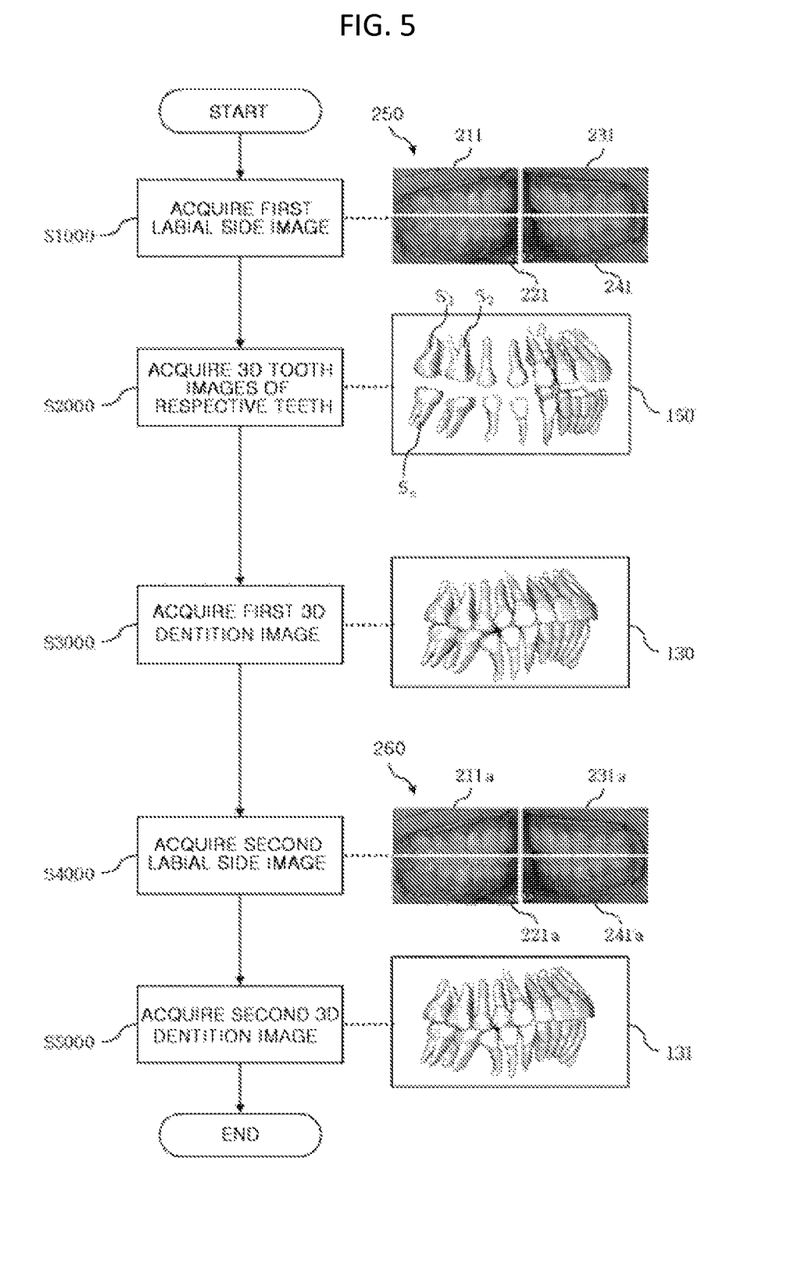
FIG. 5 is a view illustrating a method for acquiring a 3D image of a set of teeth according to an embodiment of the present invention.

FIG. 5 is a view illustrating a method for acquiring a 3D image of a set of teeth according to an embodiment of the present invention.

Referring to FIG. 5, in the method for acquiring a 3D image of a set of teeth according to the embodiment of the present invention, first, the 3D labial side image 250 of a patient is acquired using the 3D dental camera 200 at step S1000.

Furthermore, the 3D labial side image 250 is produced as a single image by combining the labial side images 211, 221, 231, and 241 acquired by the respective optical cameras 210, 220, 230, and 240 of the 3D dental camera 200.

Furthermore, in the following description, the 3D labial side image 250 is defined as a first labial side image 250 for ease of description.

Next, a 3D tooth image 150 of the individual teeth of the patient is acquired using the CT scan apparatus 100 at step S2000.

Furthermore, the 3D tooth image 150 includes 3D tooth images $S_1, S_2, \ldots,$ and $S_n$ of the respective teeth of the patient.

Furthermore, the 3D tooth images $S_1, S_2, \ldots,$ and $S_n$ are acquired by performing tooth segmentation on the dental CT data of the patient, which was acquired by the CT scan apparatus 100.

Next, the 3D tooth images $S_1, S_2, \ldots,$ and $S_n$ of the respective teeth are integrated with the first labial side image and arranged in conformity with the set of teeth of the first labial side image 250, and then the first 3D dentition image 130 which includes the set of teeth of the first labial side image 250 is acquired at step S3000.

Furthermore, the integration may be performed using a variety of well-known image integration methods including, for example, image subtraction, principal axes, joint entropy, mutual information, and cross-correlation.

Furthermore, as described with reference to FIGS. 3 and 4, the first 3D dentition image 130 is an image that can show the labial side 130a and lingual side 140a of the teeth of the patent while being rotated. Furthermore, it is possible to perform treatment simulation while intentionally moving individual teeth in the first 3D dentition image 130.

Meanwhile, the first 3D dentition image 130 may be directly acquired from CT data acquired by the CT scan apparatus 100. In this case, step S1000 of acquiring the first labial side image 250 and the process of integrating the 3D tooth images $S_1, S_2, \ldots,$ and $S_n$ of the respective teeth with the first labial side image may be omitted.

Furthermore, the order of step S3000 of acquiring the first 3D dentition image 130 and step S2000 of acquiring the 3D tooth images $S_1, S_2, \ldots,$ and $S_n$ may be reversed, and step S2000 of acquiring the 3D tooth images $S_1, S_2, \ldots,$ and $S_n$ may be performed after a second labial side image 260, which will be described below, is acquired.

That is, it is sufficient if step S2000 of acquiring the 3D tooth images $S_1, S_2, \ldots,$ and $S_n$ can be performed before a second 3D dentition image 131, which will be described below, is acquired.

Next, after an observation or a treatment period, the second labial side image 260 of the patient is acquired at step S4000.

Furthermore, the second labial side image 260 is produced as a single image by combining labial side images 211a, 221a, 231a, and 241a acquired by the respective optical cameras 210, 220, 230, and 240 of the 3D dental camera 200.

Next, the 3D tooth images $S_1, S_2, \ldots,$ and $S_n$ of the individual teeth of the patient, which were acquired before the treatment or the observation, are integrated with the second labial side image 260 and arranged in conformity of the set of teeth of the second labial side image 260, and then the second 3D dentition image 131 which includes the set of teeth of the second labial side image 260 is acquired at step S5000.

Next, the first 3D dentition image 130 and the second 3D dentition image 131 are displayed at the same time such that a practitioner can detect any change in the set teeth between the first 3D dentition image 130 and the second 3D dentition image 131.

That is, in the method for acquiring a 3D image of a set of teeth according to the embodiment of the present invention, the 3D tooth images $S_1, S_2, \ldots,$ and $S_n$ of the individual teeth of the patient, which are acquired using a single CT scan, are integrated with a changing labial side image and thus rearranged, so that the plurality of 3D images of the set of teeth 131 and 132, in which the arrangement of the teeth has changed, can be easily acquired.

Figure 6:
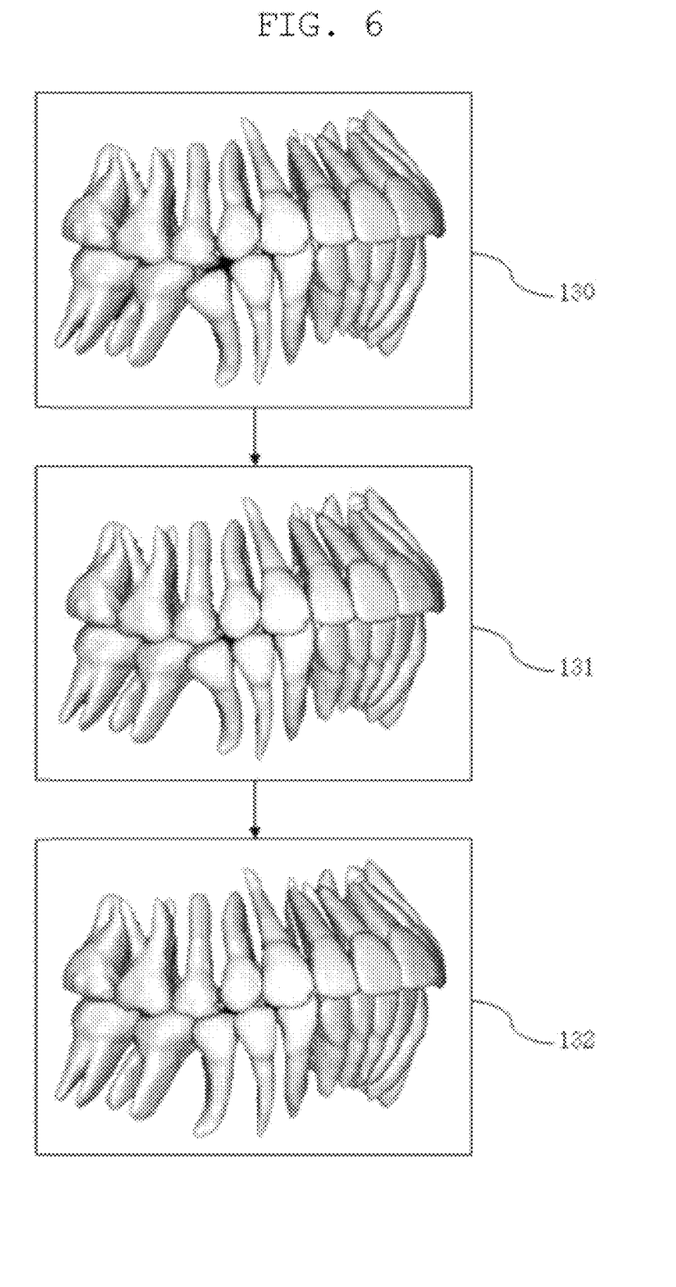
FIG. 6 is a view showing 3D images of a set of teeth that are acquired at time intervals using the method for acquiring a 3D image of a set of teeth according to the embodiment of the present invention.

FIG. 6 is a view showing 3D images of a set of teeth that are acquired at time intervals using the method for acquiring a 3D image of a set of teeth according to the embodiment of the present invention.

Referring to FIG. 6, it can be seen that the first 3D dentition image 130 showing the initial dental arrangement of a patient, the second 3D dentition image 131 showing the dental arrangement two months later, and the third 3D dentition image 132 showing the dental arrangement four months later can be acquired using the 3D tooth images $S_1, S_2, \ldots,$ and $S_n$ of the individual teeth of the patient which were acquired using a single CT scan.

Therefore, 3D images of a set of teeth that show the change of dentition can be continuously acquired using a single CT scan.

Although the present invention has been illustrated and described with reference to the preferred embodiments as described above, the present invention is not limited thereto and various variations and modifications can be performed by those having ordinary skill in the field to which the present invention pertains within the range which does not depart from the spirit of the invention.

The invention claimed is:

1. A method for acquiring a 3-Dimensional (3D) image of a set of teeth, comprising:
   acquiring 3D tooth images of respective teeth of a patient using a Computed Tomography (CT) scan;
   acquiring a first labial side image which is an optical image in which a set of teeth of the patient is shown; and
   acquiring a first 3D dentition image which includes the set of teeth of the first labial side image by integrating the 3D tooth images with the first labial side image and arranging the 3D tooth images in conformity with the set of teeth of the first labial side image.

2. The method according to claim 1, wherein the first labial side image is acquired before the acquiring the 3D tooth images.

3. The method according to claim 1, further comprising:
   after the acquiring the first 3D dentition image,
   acquiring a second labial side image of the patient after an observation or a treatment period; and
   acquiring a second 3D dentition image which includes a set of teeth of the second labial side image by integrating the 3D tooth images with the second labial side image and arranging the 3D tooth images in conformity with the set of teeth of the second labial side image.

4. The method according to claim 3, further comprising:
   after the acquiring the second 3D dentition image,
   simultaneously displaying the first 3D dentition image and the second 3D dentition image such that a change in the set of teeth between the first 3D dentition image and the second 3D dentition image can be detected.

5. The method according to claim 3, wherein each of the labial side images is acquired as a 3D labial side image using a 3D dental camera which includes a plurality of optical cameras and which can photograph all of the teeth of the patient at one time.

6. A method for acquiring a 3D image of a set of teeth, comprising:
   acquiring a first 3D dentition image of a patient using a CT scan;
   acquiring 3D tooth images of respective teeth of the patient by performing tooth segmentation on the first 3D dentition image;
   acquiring a labial side image which is an optical image in which a set of teeth of the patient is shown after an observation or a treatment period; and
   acquiring a second 3D dentition image which includes the set of teeth of the labial side image by integrating the 3D tooth images with the labial side image and arranging the 3D tooth images in conformity with the set of teeth of the labial side image.

7. The method according to claim 6, wherein the labial side image is acquired before the acquiring the 3D tooth images.

8. The method according to claim 6, further comprising:
   after the acquiring the second 3D dentition image,
   simultaneously displaying the first 3D dentition image and the second 3D dentition image such that a change in teeth between the first 3D dentition image and the second 3D dentition image can be detected.

9. The method according to claim 8, wherein each of the labial side images is acquired as a 3D labial side image using a 3D dental camera which includes a plurality of optical cameras and which can photograph all of the teeth of the patient at one time.

10. A method for acquiring a 3D image of a set of teeth, comprising:
    acquiring 3D tooth images of respective teeth of a patient using a CT scan;
    acquiring a labial side image which is an optical image in which a set of teeth of the patient is shown after an observation or a treatment period; and
    acquiring a 3D dentition image which includes the set of teeth of the labial side image by integrating the 3D tooth images with the labial side image and arranging the 3D tooth images in conformity with the set of teeth of the labial side image.

11. The method according to claim 10, wherein the labial side image is acquired as a 3D labial side image using a 3D dental camera which includes a plurality of optical cameras and which can photograph all of the teeth of the patient at one time.

12. The method according to claim 2, further comprising:
    after the acquiring the first 3D dentition image,
    acquiring a second labial side image of the patient after an observation or a treatment period; and
    acquiring a second 3D dentition image which includes a set of teeth of the second labial side image by integrating the 3D tooth images with the second labial side image and arranging the 3D tooth images in conformity with the set of teeth of the second labial side image.

13. The method according to claim 12, further comprising:
    after the acquiring the second 3D dentition image,
    simultaneously displaying the first 3D dentition image and the second 3D dentition image such that a change in the set of teeth between the first 3D dentition image and the second 3D dentition image can be detected.

14. The method according to claim 12, wherein each of the labial side images is acquired as a 3D labial side image using a 3D dental camera which includes a plurality of optical cameras and which can photograph all of the teeth of the patient at one time.

15. The method according to claim 7, further comprising:
   after the acquiring the second 3D dentition image,
   simultaneously displaying the first 3D dentition image and the second 3D dentition image such that a change in teeth between the first 3D dentition image and the second 3D dentition image can be detected.

16. The method according to claim 15, wherein each of the labial side images is acquired as a 3D labial side image using a 3D dental camera which includes a plurality of optical cameras and which can photograph all of the teeth of the patient at one time.

* * * * *